United States Patent [19]
Berry et al.

[11] Patent Number: 5,158,553
[45] Date of Patent: Oct. 27, 1992

[54] ROTATABLY ACTUATED CONSTRICTING CATHETER VALVE

[75] Inventors: Gaylord L. Berry, Salt Lake City; Lynn Kerby, Sandy, both of Utah

[73] Assignee: Cardiopulmonics, Salt Lake City, Utah

[21] Appl. No.: 633,975

[22] Filed: Dec. 26, 1990

[51] Int. Cl.⁵ .............................................. A61M 5/00
[52] U.S. Cl. .................................. 604/248; 604/246; 604/169; 604/256; 604/264
[58] Field of Search .............. 604/248, 256, 167, 246, 604/169, 164, 32, 237, 236, 264

[56] References Cited

U.S. PATENT DOCUMENTS

| | | | |
|---|---|---|---|
| 2,844,351 | 7/1958 | Smith | 604/32 X |
| 3,185,179 | 5/1965 | Harautuneian | 604/248 |
| 4,314,555 | 2/1982 | Sagae | 604/167 X |
| 4,540,411 | 9/1985 | Bodicky | 604/169 |
| 4,580,573 | 4/1986 | Quinn | 604/169 X |
| 4,978,341 | 12/1990 | Niederhauser | 604/167 |

*Primary Examiner*—John J. Wilson
*Assistant Examiner*—Jeffrey A. Smith
*Attorney, Agent, or Firm*—Workman, Nydegger, Jensen

[57] ABSTRACT

An apparatus for a catheter valve which can be used to effect selective closure of a catheter lumen in order to control fluid flow through the catheter lumen once the catheter is inserted into a patient's body. The apparatus has a valve body with a hub which is joined to the catheter, and a rotatable cap which is joined to the hub. An elastomeric sleeve is positioned in an opening through the interior of the valve body. One end of the elastomeric sleeve is joined to the rotatable cap while the other end of the elastomeric sleeve is joined to the hub. When the cap is rotated in one direction to a first position, the circular opening of the sleeve is fully opened. When the cap is rotated in the opposite direction to a second position, the elastomeric sleeve is twisted intermediate the two ends so as to ultimately effect closure of the circular opening. Due to the elastomeric properties of the sleeve, the circular opening through the sleeve tends to be uniformly constricted as the cap is rotated to effect closure.

24 Claims, 4 Drawing Sheets

ROTATABLY ACTUATED CONSTRICTING CATHETER VALVE

BACKGROUND

1. Field of the Invention

The present invention relates to an apparatus for a catheter valve which can be used to limit or prevent the loss of body fluid from a patient's body when the catheter is introduced into the patient's body, or which can be used to otherwise control the injection or removal of fluids through the catheter.

2. Technological Background

There are many types of medical devices which must be inserted into a patient's body, such as tubes, catheters, needles, introducer sheaths and the like. As used herein, the term "catheter" is intended to embrace within its scope any devices through which fluids are intended to be injected into a patient's body or through which there is the potential for removal or loss of body fluid from the patient's body, including by way of example but not limitation, tubes, catheters, needles, or introducer sheaths through which catheters, needles or other medical devices can be introduced into a patient's body.

When using such catheter-type devices, it is typically necessary or desireable to either control the injection of fluids into the patient's body or to control, limit or prevent fluids from escaping through the lumen of the catheter-type device. To this end, there are many types of clamping or valving apparatus which have been devised. For example, there are clamps or hemostats which can be placed on the outside and used to open or close tubes or catheters by pinching or collapsing the walls, thereby controlling fluid flow through the tube or catheter either into or out of the patient's body. These types of exterior clamps or hemostats are typically intended to maintain such tubes or catheters either fully open or fully closed. However, there are some circumstances in which it would be desireable to effect only partial closure of the lumen of the tube or catheter to permit reduced fluid flow. There are other types of circumstances where constriction of the lumen of such a tube or catheter must be effected in a manner so as to prevent loss of blood or other body fluid as another medical device is introduced through the tube or catheter into the patient's body.

It would be highly advantageous to have a valve which is capable of being used for any or all such types of fluid control through a catheter-type device.

BRIEF SUMMARY AND OBJECTS OF THE INVENTION

The present invention is directed to a novel apparatus for a catheter valve which can be used to effect selective closure of a catheter lumen in order to control fluid flow through the catheter lumen once the catheter is inserted into a patient's body. In a preferred embodiment of the invention, the valve body has a hub which is joined to a catheter-type device and a rotatable cap which is joined to the hub. An elastomeric sleeve is positioned in an opening through the interior of the valve body and one end of the elastomeric sleeve is joined to the rotatable cap while the other end of the elastomeric sleeve is joined to the hub. When the cap is rotated in one direction to a first position, the circular opening of the sleeve is fully opened. When the cap is rotated in the opposite direction to a second position, the elastomeric sleeve is twisted intermediate the two ends so as to ultimately effect closure of the circular opening of the sleeve when the cap is rotated to the second position. Due to the elastomeric properties of the sleeve, the circular opening of the elastomeric sleeve tends to be uniformly constricted as the cap is rotated to effect closure. The catheter valve of the present invention can be operated to effect full opening or full closure of the circular opening through the valve body and can also be operated to effect variable constriction of the circular opening or to engage the circumference of a tube or other medical device inserted through the circular opening so as to prevent fluid flow from passage around the circumference of the medical device.

Various advantages of the invention will be apparent from the drawings, description and claims which follow, or may be learned by the practice of the invention.

BRIEF DESCRIPTION OF THE DRAWINGS

The invention will be described with additional detail and specificity through the use of the accompanying drawings which are briefly summarized below. The drawings and accompanying detailed description depict the presently preferred embodiment and presently understood best mode of practicing the invention but are not otherwise to be considered as limiting of the invention's scope, which is set forth in the claims and which are intended to embrace within their scope equivalent instrumalities or combinations.

In the drawings, In FIG. 1 the catheter valve of the present invention is shown with the valve in a fully open position.

DETAILED DESCRIPTION OF THE PREFERRED EMBODIMENT

Reference is now made to the drawings wherein like parts are designated with like numerals throughout.

Figure 1:
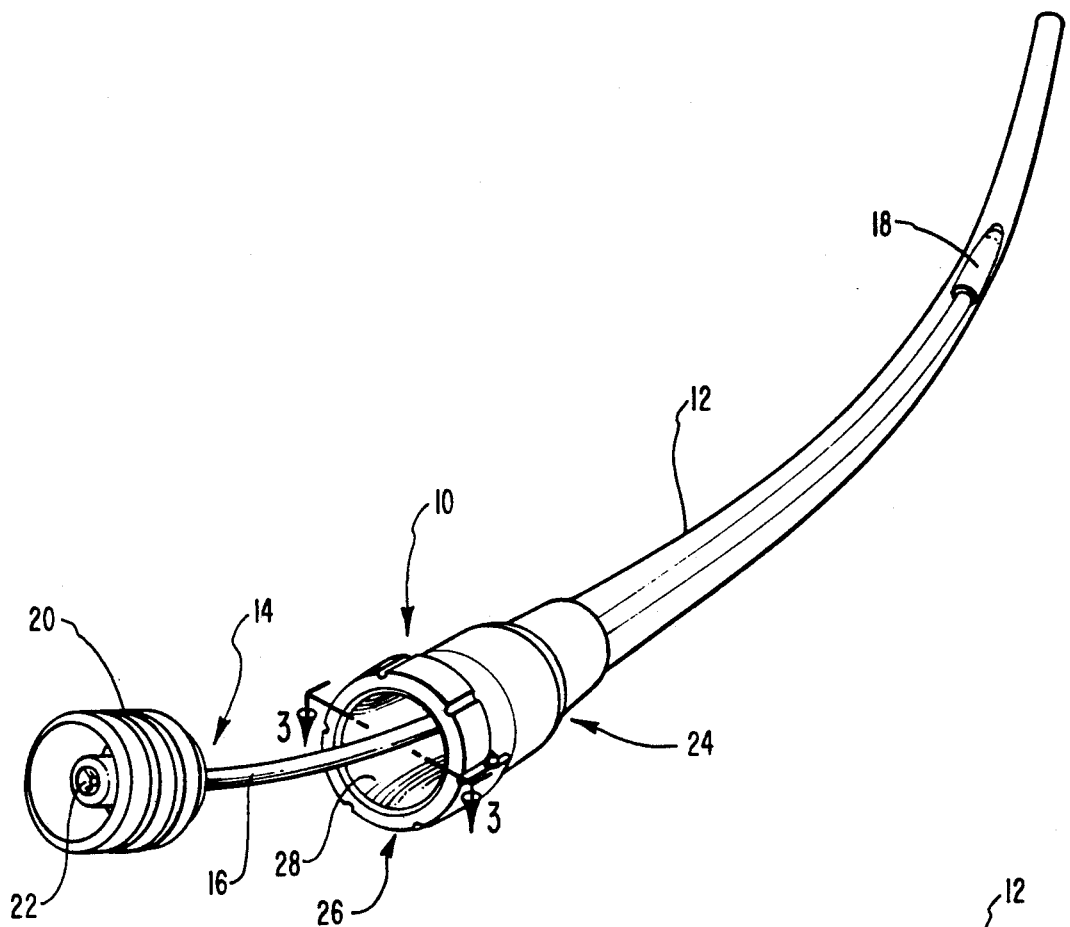
FIG. 1 is a perspective illustration showing the valve of the present invention as used with a catheter-type device, as for example an introducer sheath, with an obturator that is inserted into the introducer sheath.

Referring first to FIG. 1, the catheter valve of the present invention is generally designated at 10. For purposes of illustration only, the valve 10 is illustrated as being coupled at one end of an introducer sheath 12. In the case of the particular introducer sheath 12 which is illustrated in FIG. 1, the sheath 12 is designed particularly for insertion into the right jugular vein of a patient in order to provide access to the patient's vena cava for purposes of introducing an in vivo blood oxygenation device such as illustrated and described in U.S. Pat. No. 4,850,958. Also illustrated in connection with the introducer sheath 12 is an obturator which is generally designated at 14 and which comprises a rodlike elongated member 16 with a tip 18 connected thereto at one end (the distal end) and a gripping means 20 connected thereto at the other end (the proximal end). The obturator 14 adds stability to the sheath 10 and provides a blunt, atraumatic tip 18 to facilitate the insertion of the sheath 12 into a patient's venous system. Obturator 14 is also typically provided with a small diameter bore 22 that runs through the length of the elongated member 16 and through which a guide wire (not shown) may be threaded and which can be later used to aid in guiding the entry and positioning of a medical device such as an in vivo blood oxygenation device.

It should be understood that the sheath 12 and obturator 14 have been illustrated merely to show a typical application for which the valve of the present invention can be advantageously utilized, but is not otherwise intended to be limiting of the scope of the invention. The valve 10 may be advantageously used with any one of a variety of different types of tubes for administration of parenteral fluids, catheters for insertion into the arterial, venous or other parts of a patient's body or could be used in connection with various types of needles or other introducer sheath apparatus. Thus, as noted above, the valve of the present invention is intended to be used in connection with any such catheter-type device through which it is necessary or desireable to control, limit or prevent infusion or withdrawal of any type of fluids into or out of a patient.

With further reference to FIG. 1, in the presently preferred embodiment of the invention as illustrated in the drawings, the valve comprises a means for defining a valve body with an opening therethrough which communicates with the interior lumen of the sheath or catheter-type device to which it is connected. In the preferred embodiment, the means for defining the valve body is comprised of a hub means generally designated at 24 for joining the valve body to the elongated sheath 12 and is also comprised of a cap means as generally designated at 26 for rotatably joining said hub means. A circular opening 28 is provided through the interior of the valve body so as to provide fluid flow through the interior of the valve body. The circular opening 28 is shown in greater detail in FIG. 3.

Figure 3:
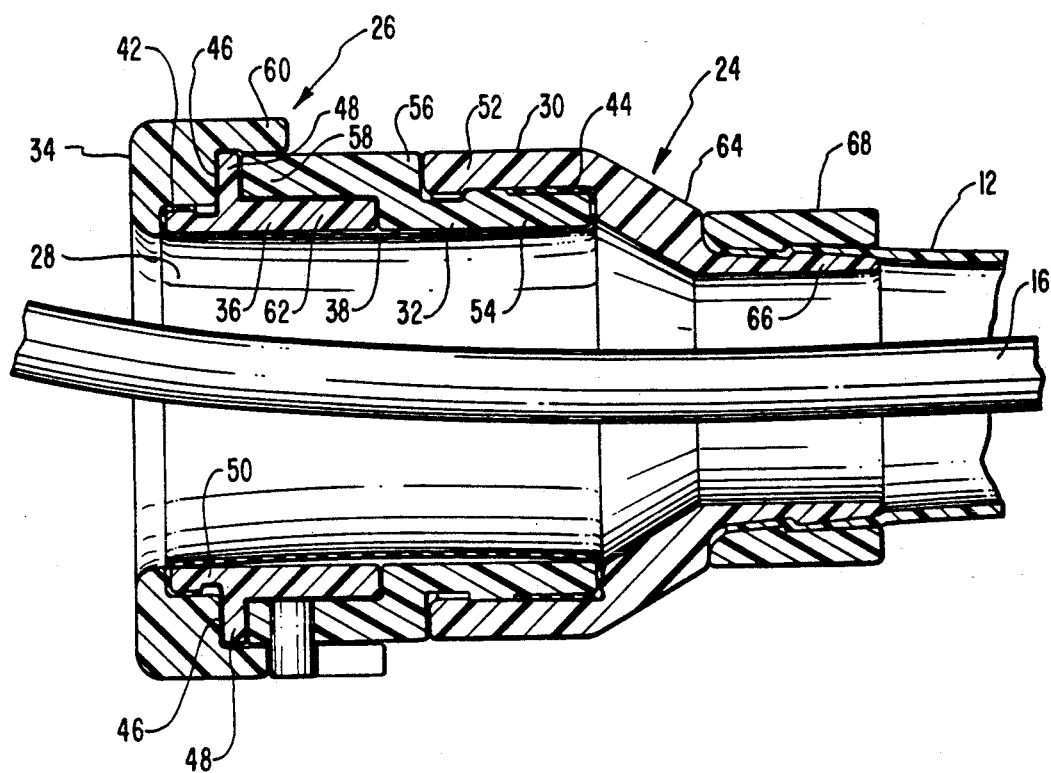
FIG. 3 is an enlarged cross-sectional view taken along line 3—3 of FIG. 1.

With further reference to FIG. 3, in the presently preferred embodiment of the invention as illustrated, the hub means 24 is comprised of an outer cylindrical sleeve clamp 30 and an inner cylindrical sleeve clamp 32. Similarly, the rotatable cap means 26 is also comprised of an outer cylindrical sleeve clamp 34 and an inner cylindrical sleeve clamp 36. In a further aspect of the invention, the valve is comprised of a means for constricting the circular opening 28 through the valve body as the cap means 26 is rotated relative to the hub means 24 such that when the cap means 26 is rotated to a first position the means for constricting does not obstruct the circular opening 28, and when the cap means 26 is rotated in an opposite direction to a second position, the means for constricting effects closure of the circular opening 28.

Figure 2:
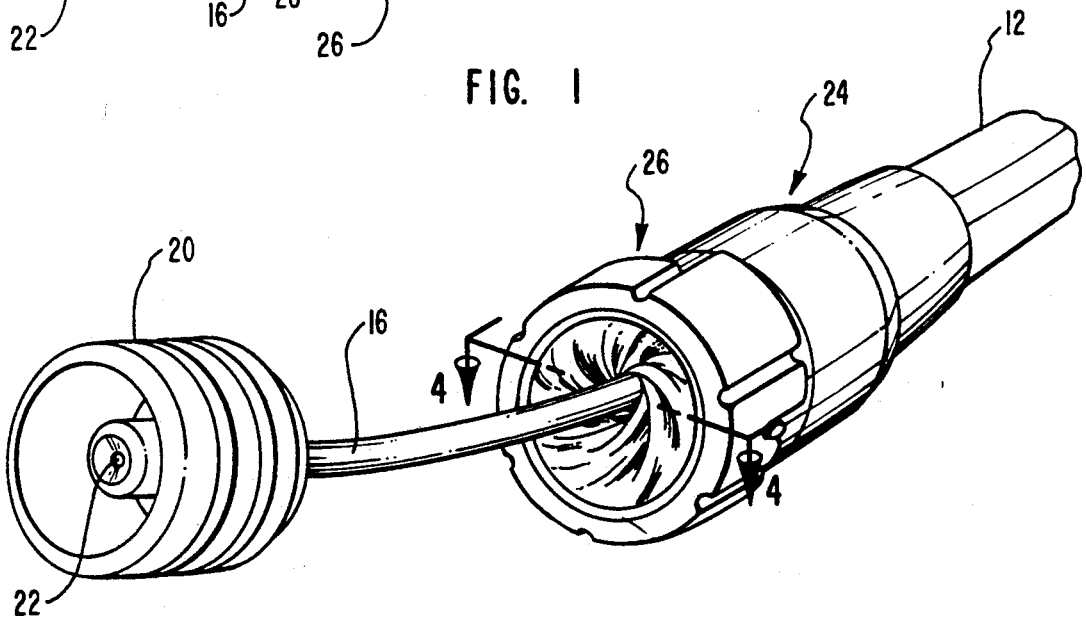
FIG. 2 is a perspective illustration showing the catheter valve of the present invention rotated to effect closure of the circular opening through the valve body so as to prevent fluid from flowing through the valve body around the obturator.
Figure 4:
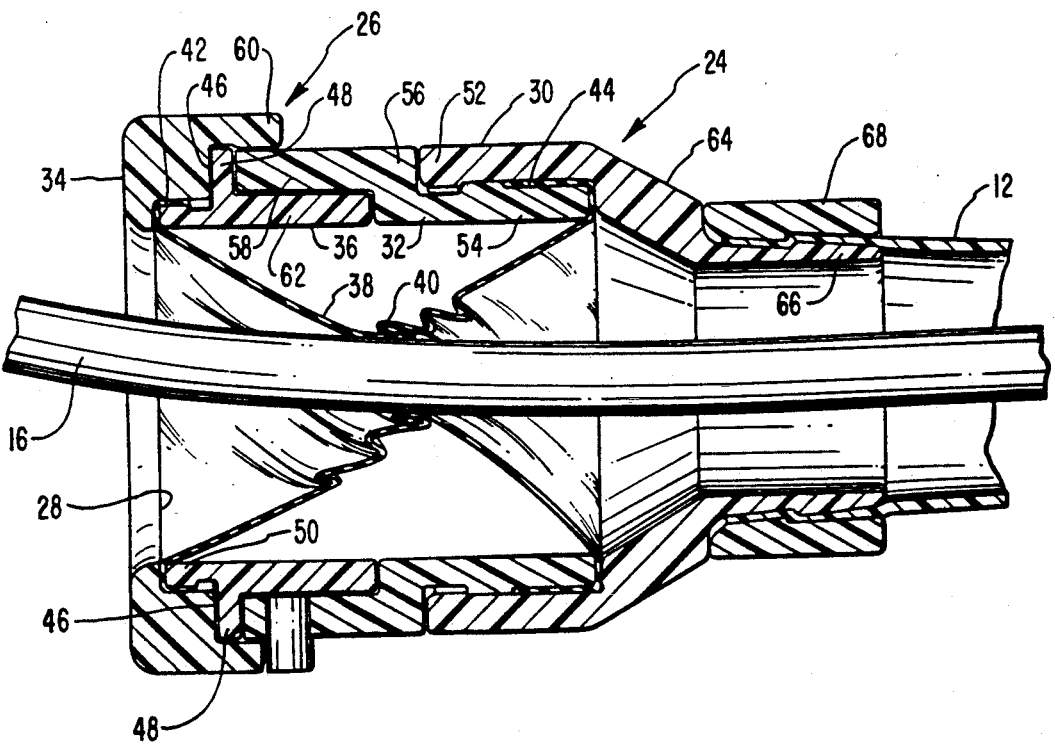
FIG. 4 is an enlarged cross-sectional view taken along line 4—4 of FIG. 2.

In the presently preferred embodiment, as shown best in FIGS. 2-4 taken together, the means for constricting the circular opening of the valve body is comprised of an elongated, cylindrical elastomeric sleeve 38. Sleeve 38 has one end 42 which is clamped and held firmly between the outer and inner cylindrical sleeve clamps 34 and 36 of rotatable cap means 26, whereas the other end 44 of the elastomeric sleeve 38 is firmly clamped and held between the outer and inner cylindrical sleeve clamps 30 and 32 of the hub means 24. Accordingly, when the cap means 26, including the outer and inner cylindrical sleeve clamps 34 and 36 are rotated while the outer and inner cylindrical sleeve clamps 30 and 32 of the hub means 24 are held stationary, the elastomeric sleeve 38 is twisted intermediate the two ends 42 and 44 of sleeve 38 so as to effect closure of the opening 28 which is otherwise provided through the sleeve 38. Thus, as shown best in FIGS. 2 and 4, the elastomeric sleeve 38 will be collapsed upon the elongated member 16 of the obturator to provide a fluid-tight seal thereby preventing any fluid from flowing through the opening 28 in the space around the elongated member 16 of the obturator. In the alternative, if an obturator or other tube or catheter-type device is not inserted through the circular opening 28 of the valve body, the elastomeric sleeve 38 can be completely collapsed to effect full closure as illustrated, for example, in the elevated end view of FIG. 6F.

With continued reference to the cross-sectional views of FIGS. 3 and 4, the outer cylindrical sleeve clamp 34 of the rotatable cap means 26 is provided with a square shoulder 46. The vertical edge of the square shoulder 46 provides a supporting abutment for a circular rim 48 that is formed on the inner cylindrical sleeve clamp 36. A portion 50 of the inner cylindrical sleeve clamp 36 extends beneath the horizontal edge of the square shoulder 46 of outer cylindrical sleeve clamp 34. The end 42 of elastomeric sleeve is firmly clamped and held between the horizontal edge of shoulder 46 and the portion 50 of inner cylindrical sleeve clamp 36 that extends therebeneath.

The opposite end 44 of the elastomeric sleeve 38 is firmly held and clamped between a horizontal extension 52 of the outer cylindrical sleeve clamp 30 and a lower horizontal extension 54 of the inner cylindrical sleeve clamp 32 of the hub means 24. The inner cylindrical sleeve clamp 32 of the hub means 24 is also comprised of a square shoulder 56 and the vertical edge of the square shoulder 56 provides a supporting abutment for the end of the horizontal extension member 52. The inner cylindrical sleeve clamp 32 also provides an upper horizontal extension member 58 which projects beneath an overhanging lip 60 on the outer cylindrical sleeve clamp 34 of the rotatable cap means 26. Further, the inner cylindrical sleeve clamp 36 of the rotatable cap means 26 also has a horizontal support member 62 which provides a rotational bearing surface upon which the upper horizontal extension member 58 rests. The outer and inner cylindrical sleeve clamps 34 and 36 of the rotatable cap means 26 are firmly bonded or otherwise secured together so as to provide a unitary piece which rotates relative to the inner and outer cylindrical sleeve clamps 30 and 32 of the hub means 24.

Because of the rotatable bearing surface provided by the horizontal support member 62 which supports the horizontal extension member 58, the outer cylindrical sleeve clamp 34 can be grasped and rotated in either direction therefore rotating both the inner and outer cylindrical sleeve clamps 34 and 36 relative to the outer and inner sleeve clamps 30 and 32 of the hub means 24. The effect of this rotational movement will be to twist the elastomeric sleeve 38 such as illustrated at point 40 thereby collapsing the elastomeric sleeve 38 at that point. In this manner, the elastomeric sleeve 38 will serve as a means for constricting the circular opening in an essentially uniform, variable fashion, as illustrated best in the elevated end views of FIGS. 6B, 6D and 6F.

Figure 6B:
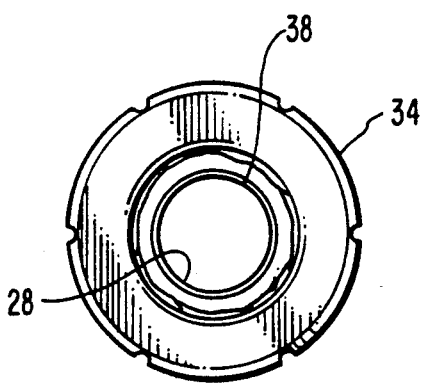
FIG. 6A is an elevated side view of the catheter valve of the present invention which illustrates the rotatable valve cap at a first position wherein the circular opening of the valve body is fully open as illustrated in the corresponding elevated end view of FIG. 6B.
FIGS. 6C and 6D are elevated side and end views, respectively, which particularly illustrate the rotatable valve cap rotated to an intermediate position so as to effect partial closure of the circular opening.
FIGS. 6E and 6F are elevated side and end views, respectively, which particularly illustrate the rotatable valve cap rotated to a second position to effect full closure of the circular opening through the valve body.
Figure 6A:
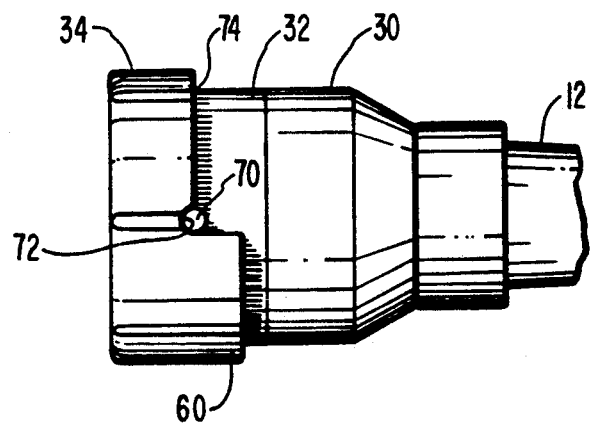
Figure 6D:
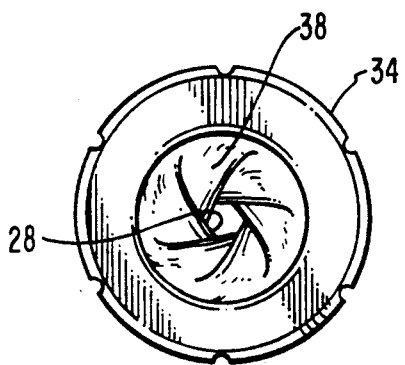
Figure 6C:
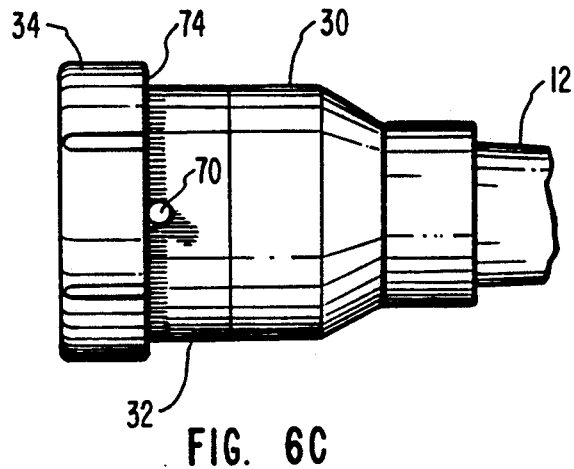
Figure 6F:
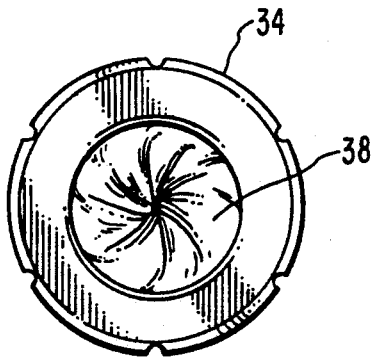
Figure 6E:
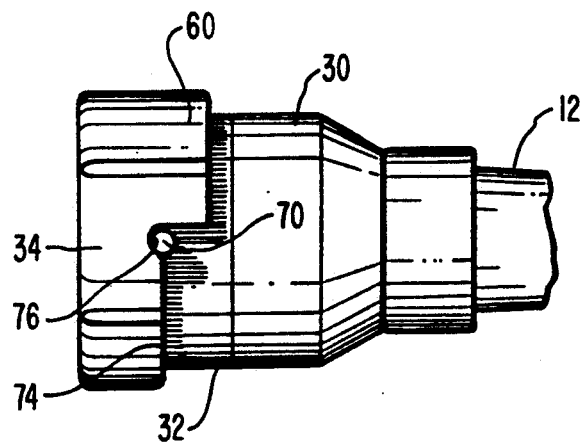

In FIG. 6B the elastomeric sleeve is not rotated so that the circular opening 28 is fully open. In FIG. 6D the rotatable cap means has been partially rotated to effect partial closure of the circular opening 28 by causing a partial collapse of the elastomeric sleeve 38 at point 40 due to the twisting effect of rotating one end of the sleeve 38 relative to the other. In FIG. 6F full closure of the circular opening has been effected by completely rotating one end of the elastomeric sleeve 38 relative to the other until the elastomeric sleeve has been completely twisted to a closed condition.

Figure 5:
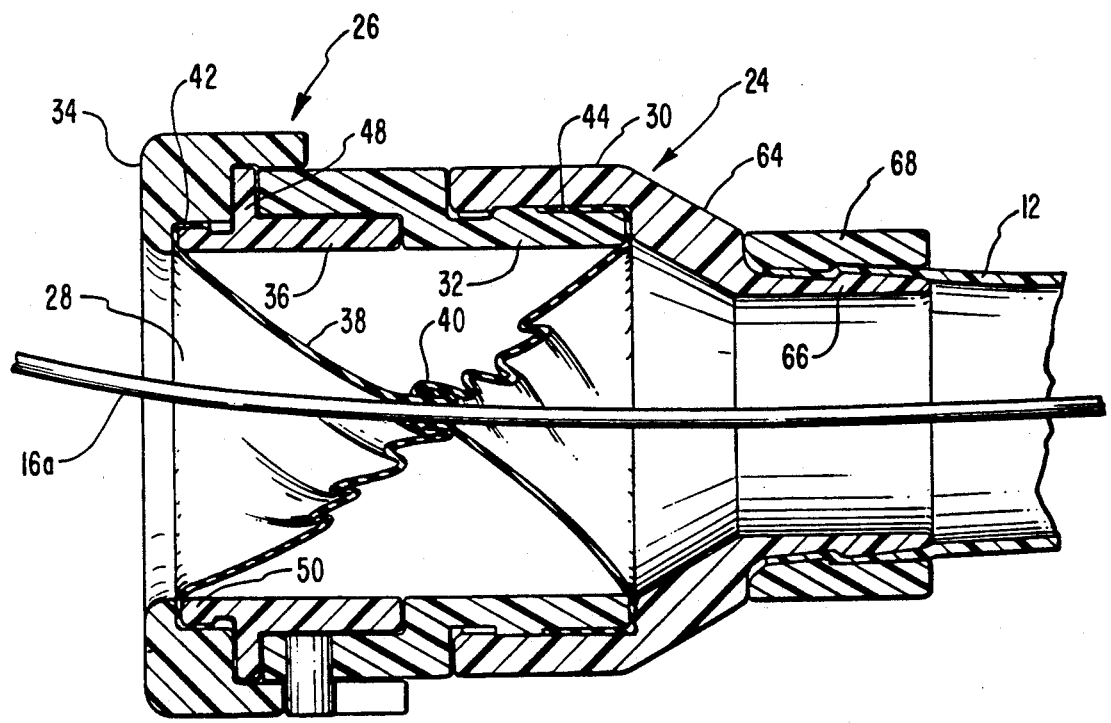
FIG. 5 is a cross-sectional view similar to that of FIG. 4, but showing a smaller diameter obturator, catheter or tube and particularly illustrating the manner in which the circular opening of the catheter valve is uniformly and variably constricted to effect closure about the circumference of the device.

As will be further appreciated in reference to FIGS. 2-5, the elastomeric sleeve 38 can also provide effective closure and fluid-tight seal against an obturator or other tube-like device which is inserted through the circular opening 28. In the case of FIGS. 2-4, the elongated rod-like member 16 of the obturator can be left free to slide in or out of the circular opening when the elastomeric sleeve 38 is in an open or partially closed condition, or alternatively the elastomeric sleeve 38 can be twisted to effect closure and to provide a fluid-tight seal against the elongated rod-like member 16 by the aforementioned rotational movement of the cap means 26 relative to the hub means 24. FIG. 5 illustrates how a tube or rod of smaller diameter such as illustrated at 16A can also be effectively sealed within the circular opening 28 by twisting one end of the elastomeric sleeve 38 relative to the other.

With further reference to FIGS. 3 and 4, the outer cylindrical sleeve clamp 30 is tapered at portion 64 and terminates in a cylindrical inner collar 66. A cylindrical outer collar 68 fits over the inner collar 66 and is used to clamp the end of the sheath or other catheter-like device 12 between the two so as to join the hub means 24 to the sheath or catheter-like device 12.

The manner of operating the valve of the present invention is best understood in reference to FIGS. 6A-6F. As will be seen best in the elevated side views of FIGS. 6A, 6C and 6E, the outer cylindrical sleeve clamp 34 also serves as a cap which can be rotated relative to the hub of the valve. The rotatable cap has a lip 60 which extends partially around the circumference of the valve. At one end of the lip 60 there is a notch 72 provided which defines a first position for the rotatable cap. At the other end of the lip 60, a shown best in FIG. 6E, there is a second notch 76 which is formed, which defines a second position of the rotatable cap. A post 70 (see also FIGS. 3 and 4) is anchored in the inner cylindrical sleeve clamp 32 of the hub means.

Post 70 in conjunction with the lip 60 serves as a stop means for limiting rotational movement of the rotatable cap in either direction of rotation. Accordingly, when the rotatable cap is rotated to the position shown in FIG. 6A, the elastomeric sleeve 38 is fully open so as not to obstruct the circular opening 28 of the valve body. When the rotatable cap is partially rotated as shown in FIG. 6C the elastomeric sleeve 38 will partially constrict as it begins to twist at the intermediate portion of its length. Thus, as shown in FIG. 6D the circular opening 28 will be partially obstructed when the cap is rotated to the position of FIG. 6C. When the rotatable cap is fully rotated in the opposite direction to the notch 76 so that the rotatable cap will be held in that position by the post 70, the elastomeric sleeve 38 will effect full closure of the circular opening 28, as shown in FIG. 6F. As will be further appreciated from FIGS. 6A, 6C and 6E taken together, the rotatable cap has a portion of its length shortened as illustrated at 74 so as to permit rotation of the cap relative to the post 70 which provides a stop for engaging the notched positions 72 or 76.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A valve for effecting selective closure of a catheter lumen to control fluid flow through said catheter lumen once a catheter is inserted into a patient's body, said valve comprising:

means for defining a valve body with an inside opening therethrough which communicates with said catheter lumen, said means for defining said valve body comprising hub means for joining said valve body to said catheter, and cap means for rotatably joining to said hub means, and the hub means and cap means each comprising a clamping means; and means for constricting said inside opening of said valve body as said cap means is rotated relative to said hub means and said means for constricting having one end wrapped around and clamped by the clamping means of the hub means, and having another end wrapped around and clamped by the clamping means of the cap means, so as to provide an unobstructed lining along said inside opening of said valve body, such that when said cap means is rotated to a first position said means for constricting does not obstruct said inside opening, and when said cap means is rotated to a second position, said means for constricting effects closure of said inside opening of said valve body.

2. A valve as defined in claim 1 wherein said clamping means of the hub means comprises an outer cylindrical sleeve clamp and an inner cylindrical sleeve clamp.

3. A valve as defined in claim 2 wherein said clamping means of the cap means comprises an outer cylindrical sleeve clamp and an inner cylindrical sleeve clamp.

4. A valve as defined in claim 3 wherein said means for constricting said opening comprises a cylindrical, elastomeric sleeve having one end clamped between the inner and outer sleeve clamps of said hub means, and having another end clamped between the inner and outer sleeve clamps of said cap means, such that when said cap means is rotated relative to said hub means to a first position, said elastomeric sleeve is untwisted and open, and when said cap means is rotated relative to said hub means to a second position, said elastomeric sleeve is twisted to effect closure of the sleeve.

5. A valve as defined in claim 2 wherein said hub means further comprises a cylindrical catheter clamp.

6. A valve as defined in claims 1 or 2 further comprising stop means for limiting rotation of said cap means relative to said hub means so as to stop said cap means at said first position when rotated in one direction, and so as to stop said cap means at said second position when rotated in an opposite direction.

7. A valve as defined, in claim 6 wherein said stop means comprises:
 a post anchored in the inner cylindrical sleeve clamp of said hub means; and a lip extending around a portion of the circumference of said outer cylindrical sleeve clamp of said cap means.

8. A valve for controlling fluid flow through a catheter connected to said valve when said catheter is inserted into a blood vessel, said valve comprising:
 a valve body having an inside opening, said valve body comprised of a hub means for joining said valve to said catheter and a cap means for rotatably joining to said hub means, said hub means and said cap means each comprising a means for clamping an end of a cylindrical elastomeric sleeve, said cylindrical, elastomeric sleeve having one end wrapped around one of said clamping means and clamped to said hub means, and having another end wrapped around the other said clamping means and clamped to said cap means, such that when said cap means is rotated relative to said hub means to a first position, said cylndrical elastomeric sleeve is untwisted and open and provides an uninterrupted, seamless lining along said inside opening of said valve body, and when said cap means is rotated relative to said hub means to a second position, said cylindrical elastomeric sleeve is twisted to effect closure of said opening of said valve body.

9. A valve as defined in claim 8 further comprising stop means for limiting rotation of said cap means relative to said hub means so as to stop said cap means at said first position when rotated in one direction, and so as to stop said cap means at said second position when rotated in an opposite direction.

10. A valve as defined in claim 9 wherein said stp means comprises:
 a post anchored in the inner cylindrical sleeve clamp of said hub means; and
 a lip extending around a portion of the circumference of said outer cylindrical sleeve clamp of said cap means.

11. A valve as defined in claim 10 wherein said hub means further comprises a cylindrical catheter clamp.

12. A valve as defined in claim 8 wherein each said means for clamping an end of said elastomeric sleeve comprises an outer cylindrical sleeve clamp and an inner cylindrical sleeve clamp.

13. A valve for effecting selective closure of a catheter lumen to control fluid flow through said catheter lumen once a catheter is inserted into a patient's body, said valve comprising:
 means for defining a valve body with an inside opening therethrough which communicates with said catheter lumen, said means for defining said valve body comprising hub means for joining said valve body to said catheter lumen, and cap means for rotatably joining to said hub means said catheter lumen, and the hub means and cap means each comprising a clamping means;
 means for constricting said opening of said valve body as said cap means is rotated relative to said hub means, such that when said cap means is rotated to a first position said means for constricting does not obstruct said opening and said means for constricting having one end wrapped around and clamped by the clamping means of the hub means, and having another end wrapped around and clamped by the clamping means of the cap means, so as to provide an unobstructed lining along said inside opening of said valve body, and when said valve is rotated to a second position, said means for constricting effects closure of said inside opening of said valve body; and
 stop means for limiting rotation of said cap means relative to said hub means so as to stop said cap means at said first position when said cap means is rotated in one direction, and so as to stop said cap means at said second position when said cap means is rotated in an opposite direction.

14. A valve as defined in claim 13 wherein said clamping means of the hub means comprises an outer cylndrical sleeve clamp and an inner cylndrical sleeve clamp.

15. A valve as defined in claim 14 wherein said clamping means of the cap means comprises an outer cylndrical sleeve clamp and an inner cylndrical sleeve clamp.

16. A valve as defined in claim 15 wherein said means for constricting said opening comprises a cylindrical, elastomeric sleeve having one end clamped between the inner and outer sleeve clamps of said hub means, and having another end clamped between the inner and outer sleeve clamps of said cap means, such that when said cap means is rotated relative to said hub means to a first position, said elastomeric sleeve is untwisted and open, and when said cap means is rotated relative to said hub means to a second position, said elastomeric sleeve is twisted to effect closure of the sleeve.

17. A valve as defined in claim 16 wherein said stop means comprises:
 a post anchored in the inner cylindrical sleeve clamp of said hub means; and
 a lip extending around a portion of the circumference of said outer cylindrical sleeve clamp of said cap means.

18. A valve as defined in claim 17 wherein said hub means further comprises a cylindrical catheter clamp.

19. A valve for effecting selective closure of a catheter lumen and about a tube inserted therethrough to prevent escape of body fluid through said catheter lumen when said catheter is inserted into a patient's body, said valve comprising:
 means for defining a valve body with an circular opening through the inside of said valve body and which communicates with said catheter lumen, said means for defining said valve body comprising hub means for joining said valve body to said catheter lumen, and cap means for rotatably joining to said hub means, and the hub means and cap means each comprising a clamping means; and means for variably constricting said circular opening of said valve body as said cap means is rotated relative to said hub means, said means for variably constricting having one end wrapped around and clamped by the clamping means of the hub means, and having another end wrapped around and clamped by the clamping means of the cap means so as to provide an unobstructed lining along said opening along the inside of said valve body, such that when said means is rotated to a first position said means for variably constricting said circular opening seamlessly lines the inside of said valve body but does not obstruct said circular opening so that said tube is freely slidable through said circular opening and the lumen of said catheter, and such that when said valve body is rotated to a second position said means for variably constricting said circular opening uniformly closes around said tube and frictionally engages said tube to prevent escape of body fluid through said catheter lumen and around said tube through said circular opening of said valve body.

20. A valve as defined in claim 19 further comprising stop means for limiting rotation of said cap means relative to said hub means so as to stop said cap means at said first position when rotated in one direction, and so as to stop said cap means at said second position when rotated in an opposite direction.

21. A valve as defined in claim 20 wherein said stop means comprises:
  a post anchored in the inner cylindrical sleeve clamp of said hub means; and
  a lip extending around a portion of the circumference of said outer cylindrical sleeve clamp of said cap means.

22. A valve as defined in claim 19 wherein said clamping means of the hub means comprises an outer cylindrical sleeve clamp and an inner cylindrical sleeve clamp.

23. A valve as defined in claim 22 wherein said clamping means of the cap means comprises an outer cylindrical sleeve clamp and an inner cylindrical sleeve clamp.

24. A valve as defined in claim 23 wherein said means for constricting said opening comprises a cylindrical, elastomeric sleeve having one end clamped between the inner and outer sleeve clamps of said hub means, and having another end clamped between the inner and outer sleeve clamps of said cap means, such that when said cap means is rotated relative to said hub means to a first position, said elastomeric sleeve is untwisted and open, and when said cap means is rotated relative to said hub means to a second position, said elastomeric sleeve is twisted to effect closure of the sleeve.

* * * * *

UNITED STATES PATENT AND TRADEMARK OFFICE
CERTIFICATE OF CORRECTION

PATENT NO. : 5,158,553

DATED : October 27, 1992

INVENTOR(S) : GAYLORD L. BERRY et al.

It is certified that error appears in the above-identified patent and that said Letters Patent is hereby corrected as shown below:

```
Column 1, line 16, "sheathes" should be --sheaths--
Column 1, line 27, "desireable" should be --desirable--
Column 1, line 32, "there" should be --there are--
Column 1, line 40, "desireable" should be --desirable--
Column 2, line 31, "instrumalities" should be --instrumentalities--
Column 3, line 44, "desireable" should be --desirable--
Column 5, line 64, "a shown" should be --as shown--
Column 8, line 29, "cylndrical" should be --cylindrical--
```

Signed and Sealed this

Twelfth Day of October, 1993

*Attest:*

BRUCE LEHMAN

*Attesting Officer*     *Commissioner of Patents and Trademarks*